United States Patent
Maroscheck et al.

(10) Patent No.: US 11,806,229 B2
(45) Date of Patent: Nov. 7, 2023

(54) CONTAINER SYSTEM FOR HEATING AN INTRAOCULAR LENS

(71) Applicant: IOLUTION GMBH, Hamburg (DE)

(72) Inventors: Christoph Maroscheck, Hamburg (DE); Helmut Binder, Berlin (DE)

(73) Assignee: IOLUTION GMBH, Hamburg (DE)

( * ) Notice: Subject to any disclaimer, the term of this patent is extended or adjusted under 35 U.S.C. 154(b) by 1178 days.

(21) Appl. No.: 15/305,772

(22) PCT Filed: Apr. 20, 2015

(86) PCT No.: PCT/DE2015/000191
§ 371 (c)(1),
(2) Date: Oct. 21, 2016

(87) PCT Pub. No.: WO2015/161837
PCT Pub. Date: Oct. 29, 2015

(65) Prior Publication Data
US 2017/0042666 A1     Feb. 16, 2017

(30) Foreign Application Priority Data

Apr. 22, 2014   (DE) ..................... 10 2014 005 719.4

(51) Int. Cl.
| | |
|---|---|
| A61F 2/16 | (2006.01) |
| B65D 25/20 | (2006.01) |
| B65D 25/54 | (2006.01) |
| B65D 81/22 | (2006.01) |

(52) U.S. Cl.
CPC ............ *A61F 2/1691* (2013.01); *A61F 2/167* (2013.01); *A61F 2/1678* (2013.01); *B65D 25/20* (2013.01); *B65D 25/54* (2013.01); *B65D 81/22* (2013.01)

(58) Field of Classification Search
CPC ...... A61F 2/1678; A61F 2/1691; A61F 2/167; B65D 25/20; B65D 25/54; B65D 81/22
USPC ........ 219/385, 386, 437, 521; 422/559, 547; 606/107
See application file for complete search history.

(56) References Cited

U.S. PATENT DOCUMENTS

| | | | |
|---|---|---|---|
| 4,955,889 A | 9/1990 | Gent | |
| 6,360,883 B1 * | 3/2002 | Haq | A45C 11/005 206/205 |
| 6,398,789 B1 * | 6/2002 | Capetan | A61F 2/1691 606/107 |
| 2007/0033906 A1 | 2/2007 | Kernick et al. | |
| 2007/0168026 A1 * | 7/2007 | Nagasaka | A61F 2/1675 623/6.12 |
| 2007/0250068 A1 * | 10/2007 | Vincent-Aubry | A61F 2/1678 606/107 |

(Continued)

FOREIGN PATENT DOCUMENTS

| | | |
|---|---|---|
| CN | 101621972 A | 1/2010 |
| CN | 101180217 B | 9/2010 |

(Continued)

*Primary Examiner* — Phuong T Nguyen
(74) *Attorney, Agent, or Firm* — Smartpat PLC

(57) ABSTRACT

The present invention relates to a container system (200) for storing an intraocular lens (90). The container system (200) comprises a container (210) for storing a lens (90) and a heating device (220) for heating the lens (90) in the container (210). A heated lens (90) is more supple and can be rolled up better and smaller, such that a cut opening in an eye can be further reduced.

18 Claims, 16 Drawing Sheets

(56) References Cited

U.S. PATENT DOCUMENTS

| | | |
|---|---|---|
| 2008/0009460 A1 | 1/2008 | Linden et al. |
| 2008/0033449 A1* | 2/2008 | Cole ................ A61F 2/1664 606/107 |
| 2008/0097460 A1* | 4/2008 | Boukhny ........... A61F 2/1662 606/107 |
| 2008/0097461 A1 | 4/2008 | Boukhny et al. |
| 2009/0125034 A1* | 5/2009 | Pynson ............. A61F 2/1678 606/107 |
| 2009/0204122 A1* | 8/2009 | Ichinohe ........... A61F 2/167 606/107 |
| 2010/0258551 A1* | 10/2010 | Hadfield ........... A61L 12/086 219/428 |
| 2011/0264102 A1 | 10/2011 | Cole et al. |
| 2011/0264103 A1 | 10/2011 | Cole et al. |
| 2013/0089629 A1 | 4/2013 | Beijer et al. |
| 2015/0045805 A1 | 2/2015 | Kontur et al. |

FOREIGN PATENT DOCUMENTS

| | | | |
|---|---|---|---|
| DE | 2739788 A1 | 3/1979 | |
| DE | 3434836 A1 | 4/1986 | |
| EP | 0766496 A1 | 4/1997 | |
| FR | 2935606 A1 * | 3/2010 | ........... A61F 2/1678 |
| FR | 2980102 A1 | 3/2013 | |
| WO | 01/78566 A1 | 10/2001 | |
| WO | 2011155887 A1 | 12/2011 | |
| WO | WO-2012155887 A1 * | 11/2012 | ........... A61F 2/1678 |

\* cited by examiner

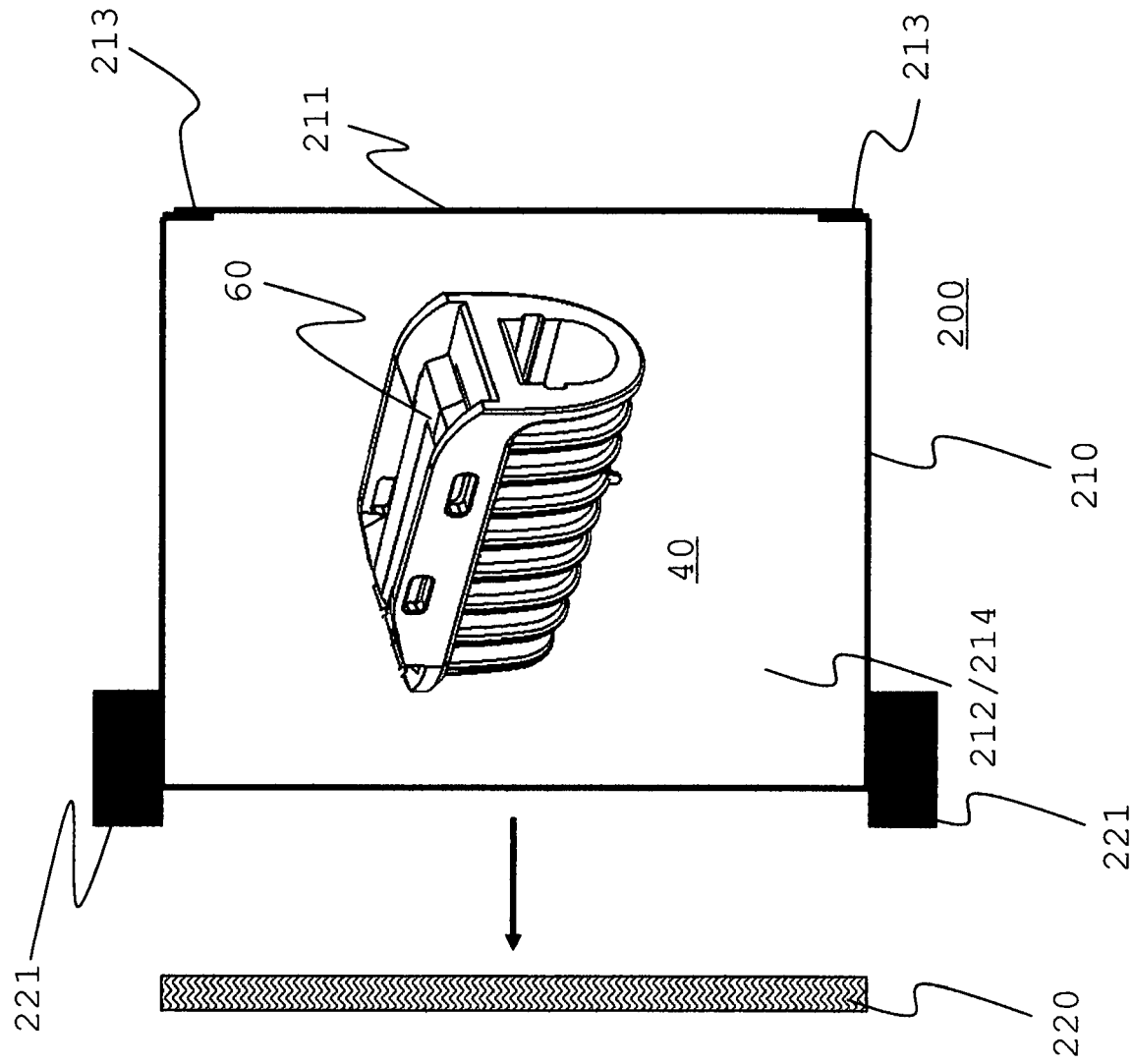
Fig. 3.a

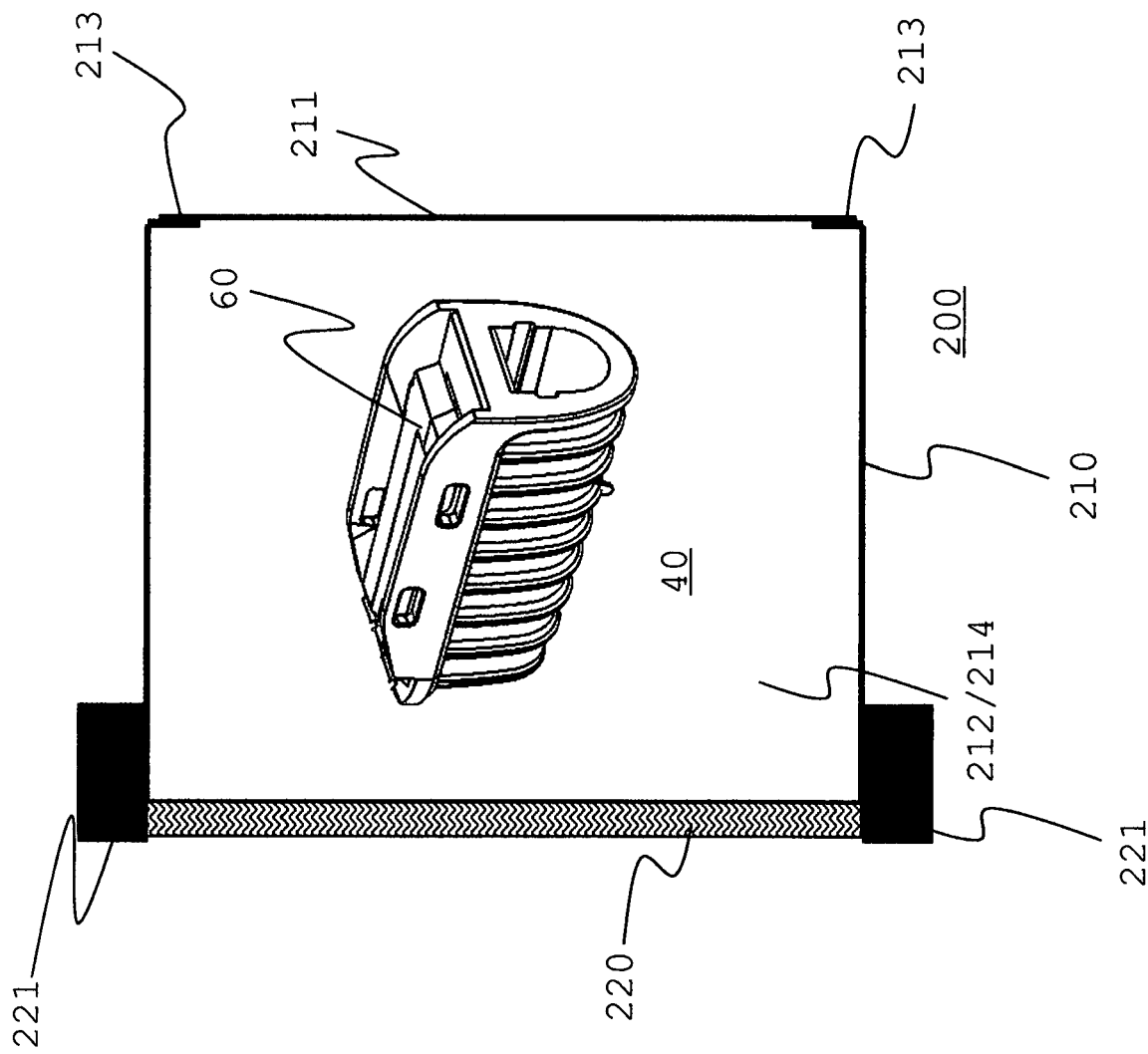
Fig. 3.b

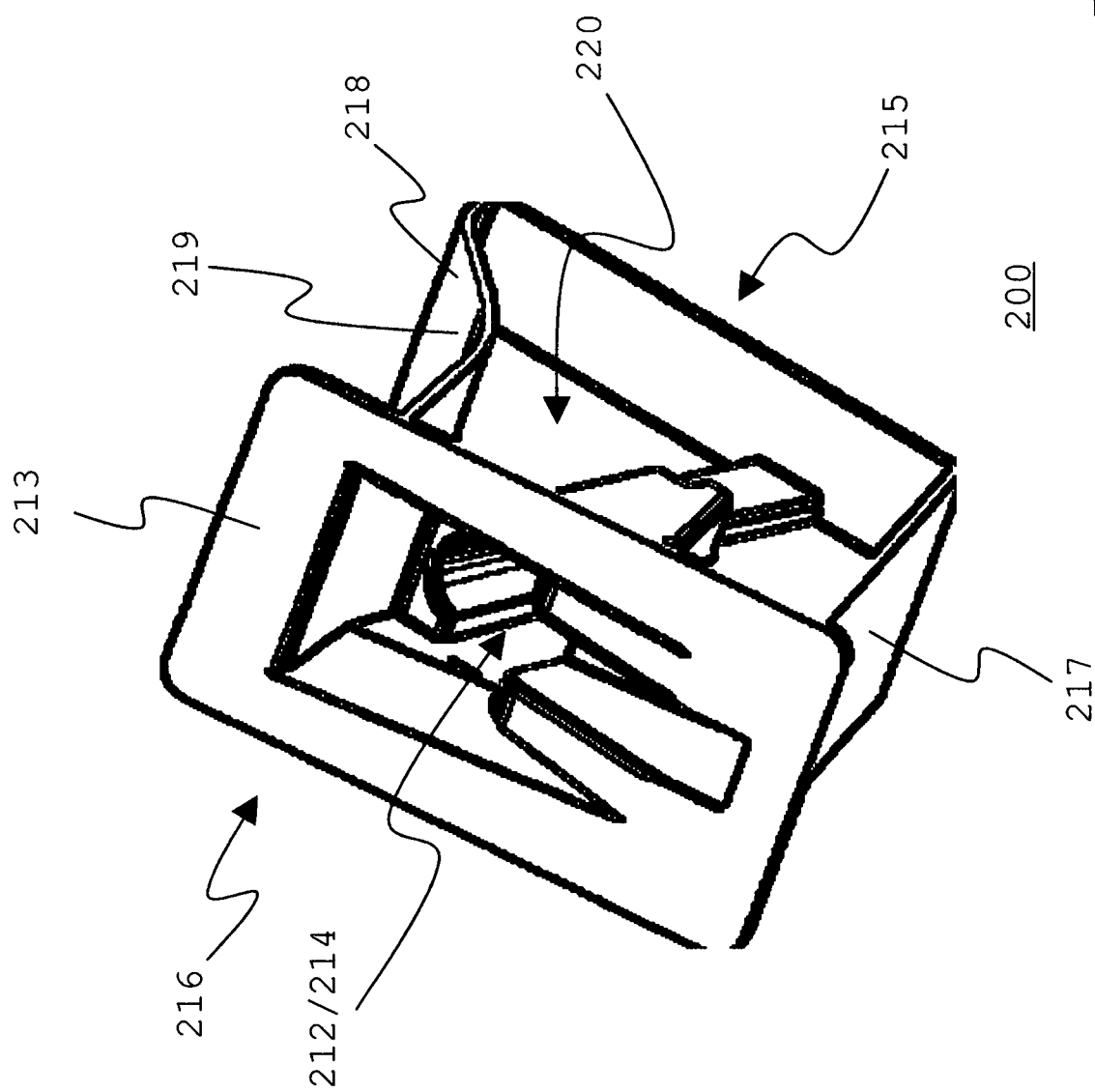
Fig. 4.a

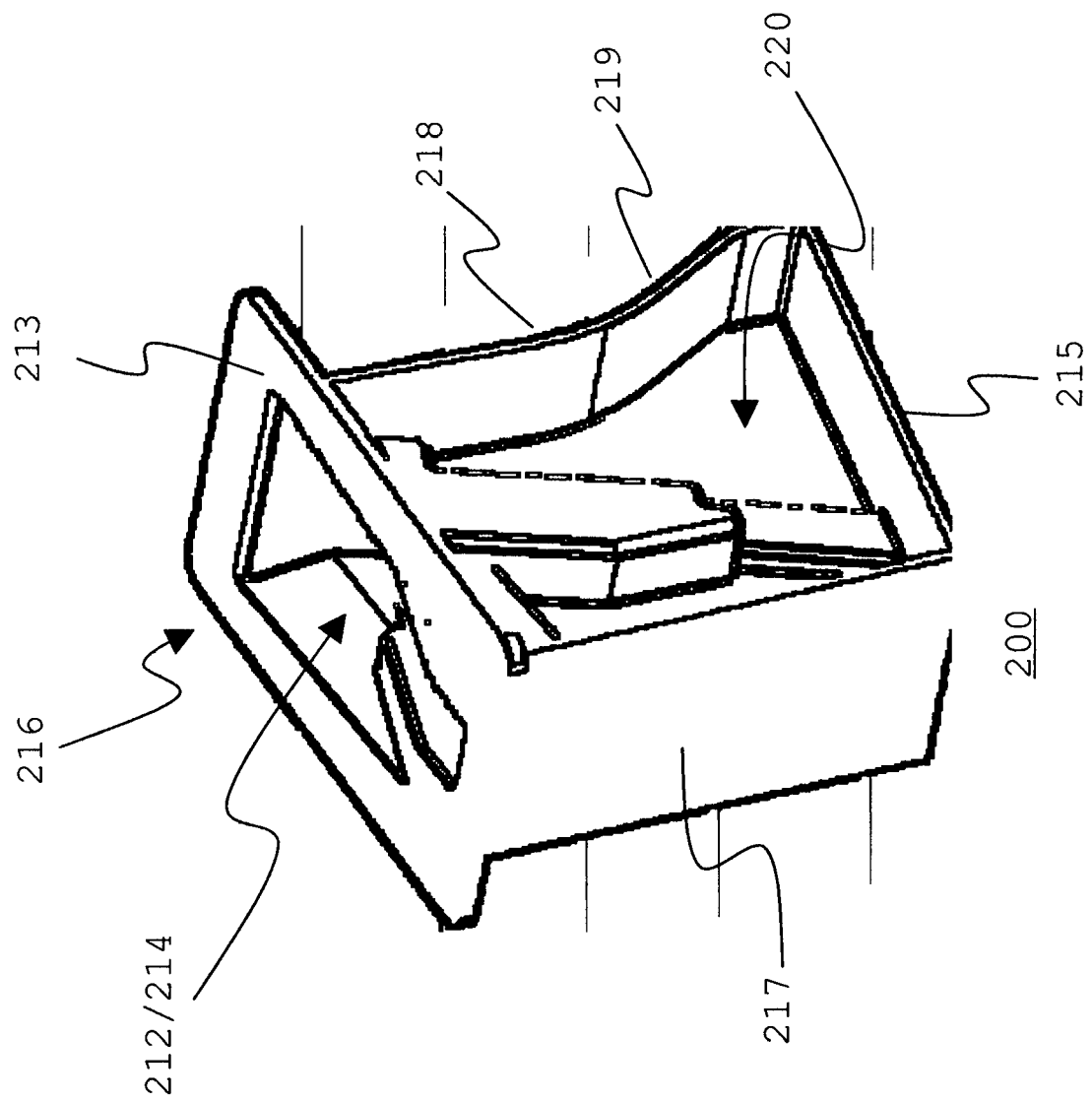
Fig. 4.b

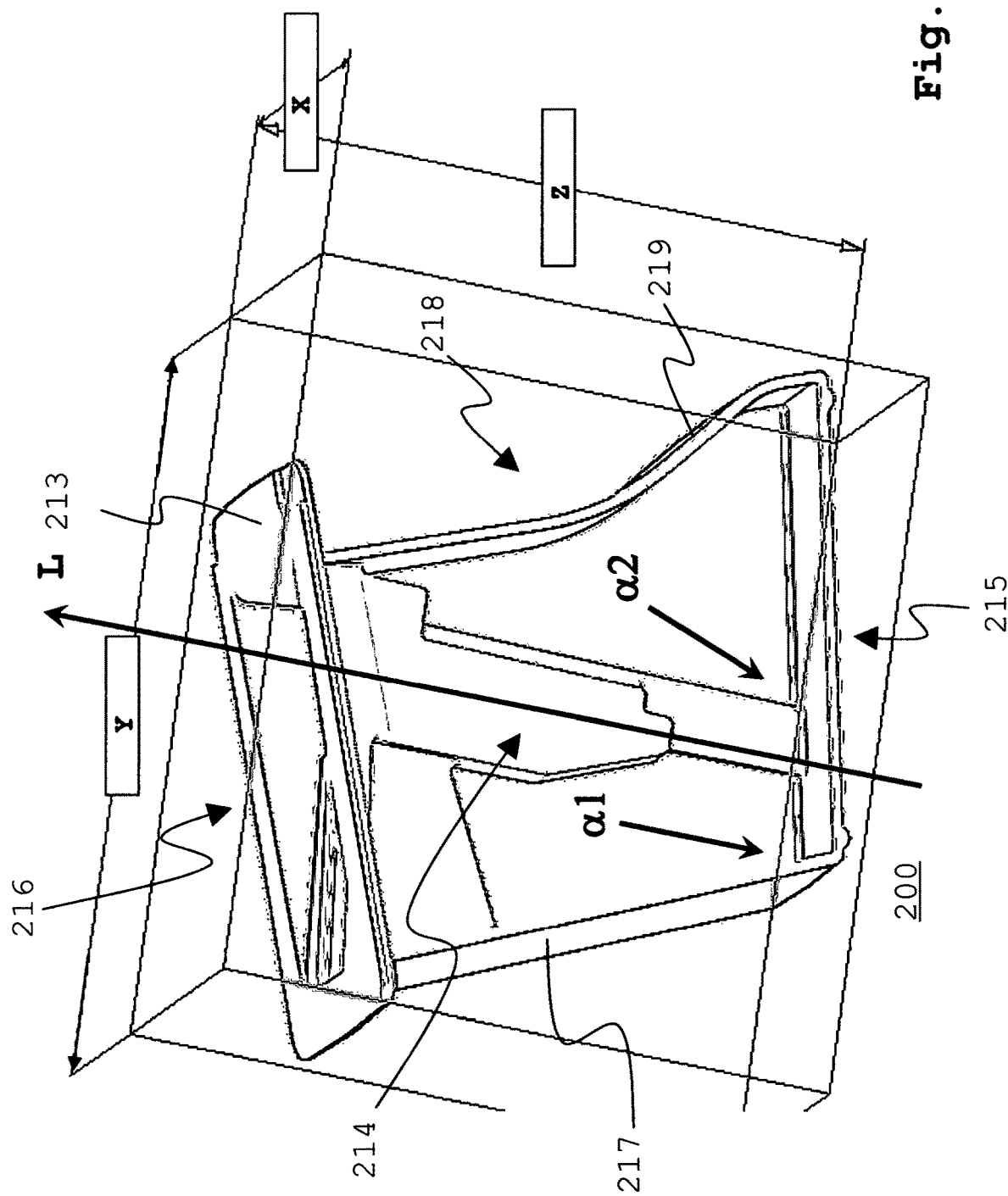

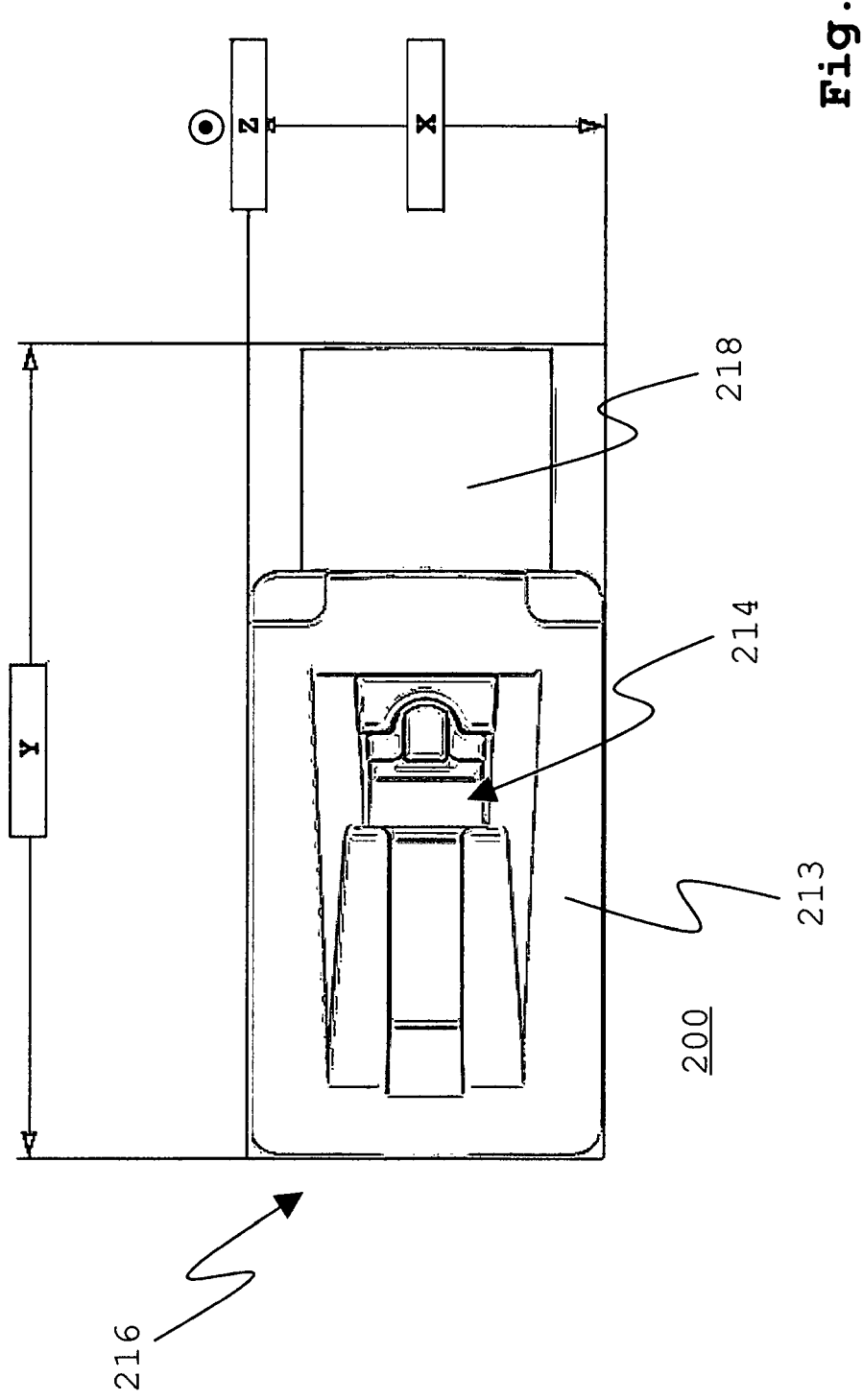

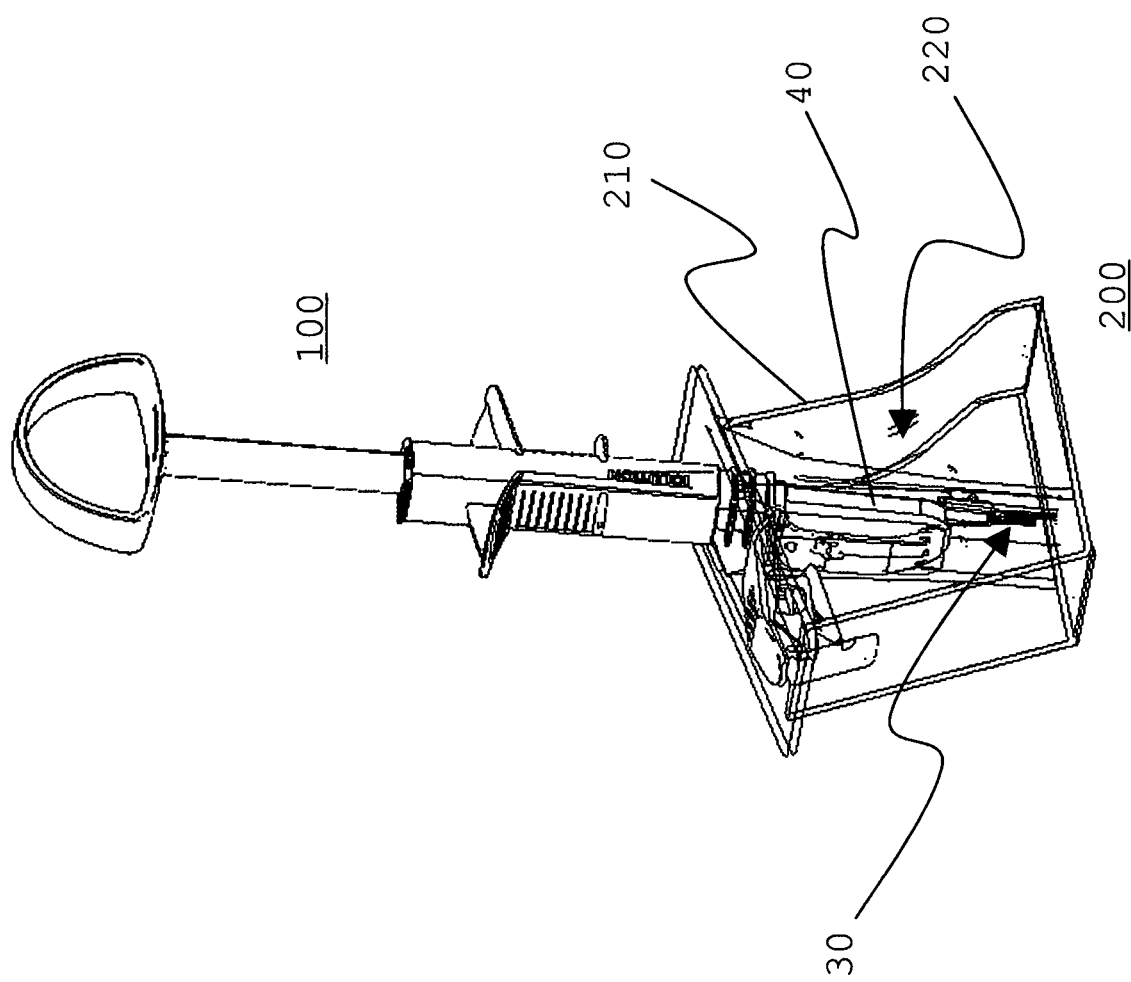
Fig. 5.a

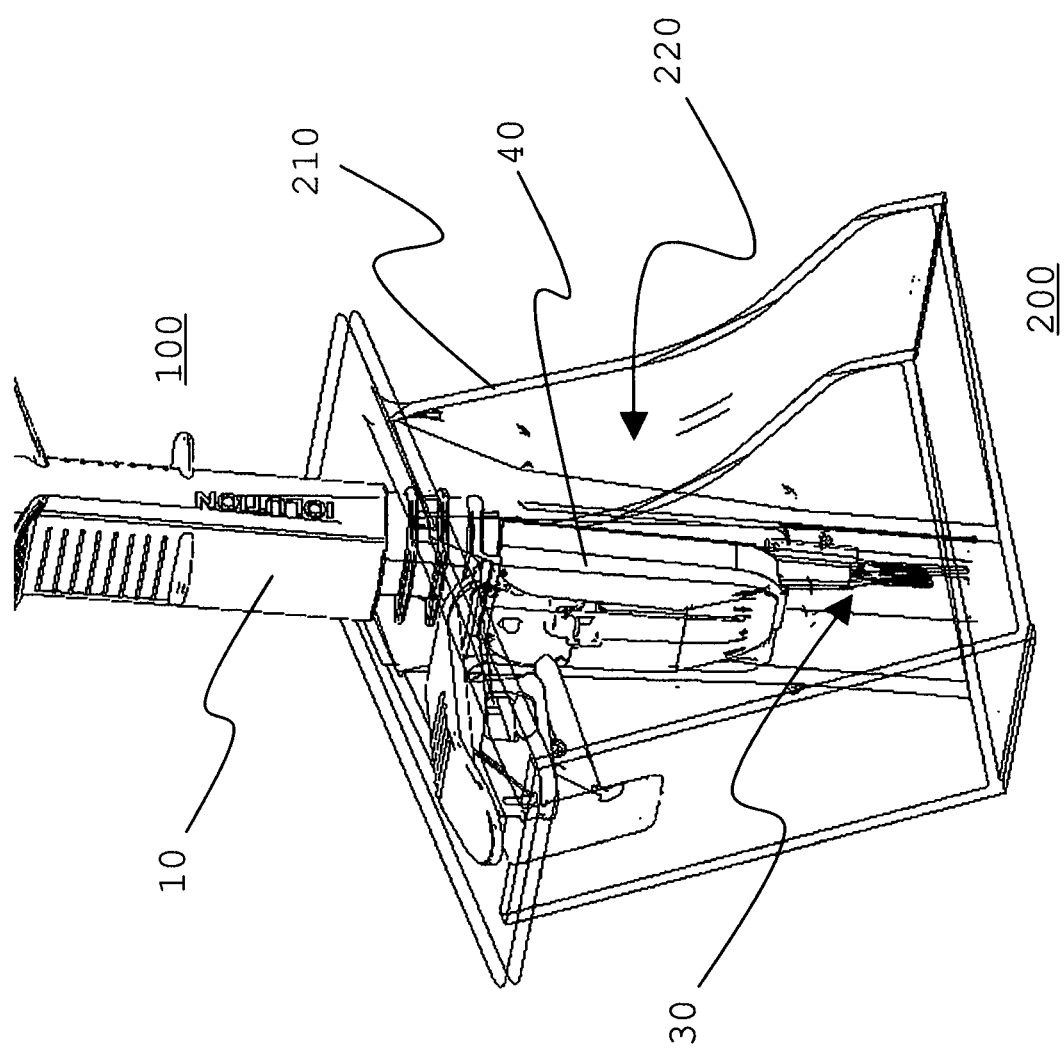
Fig. 5.b

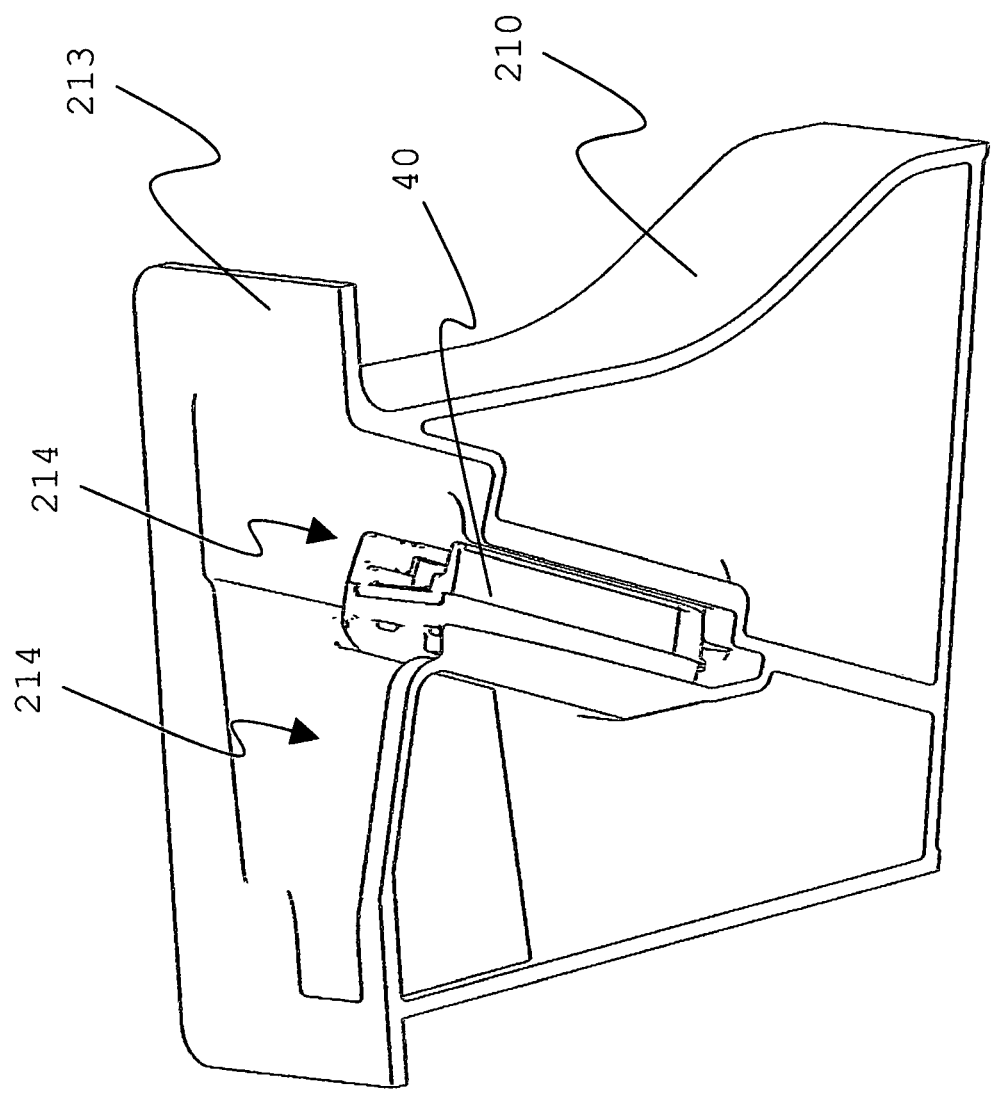
Fig. 6.a

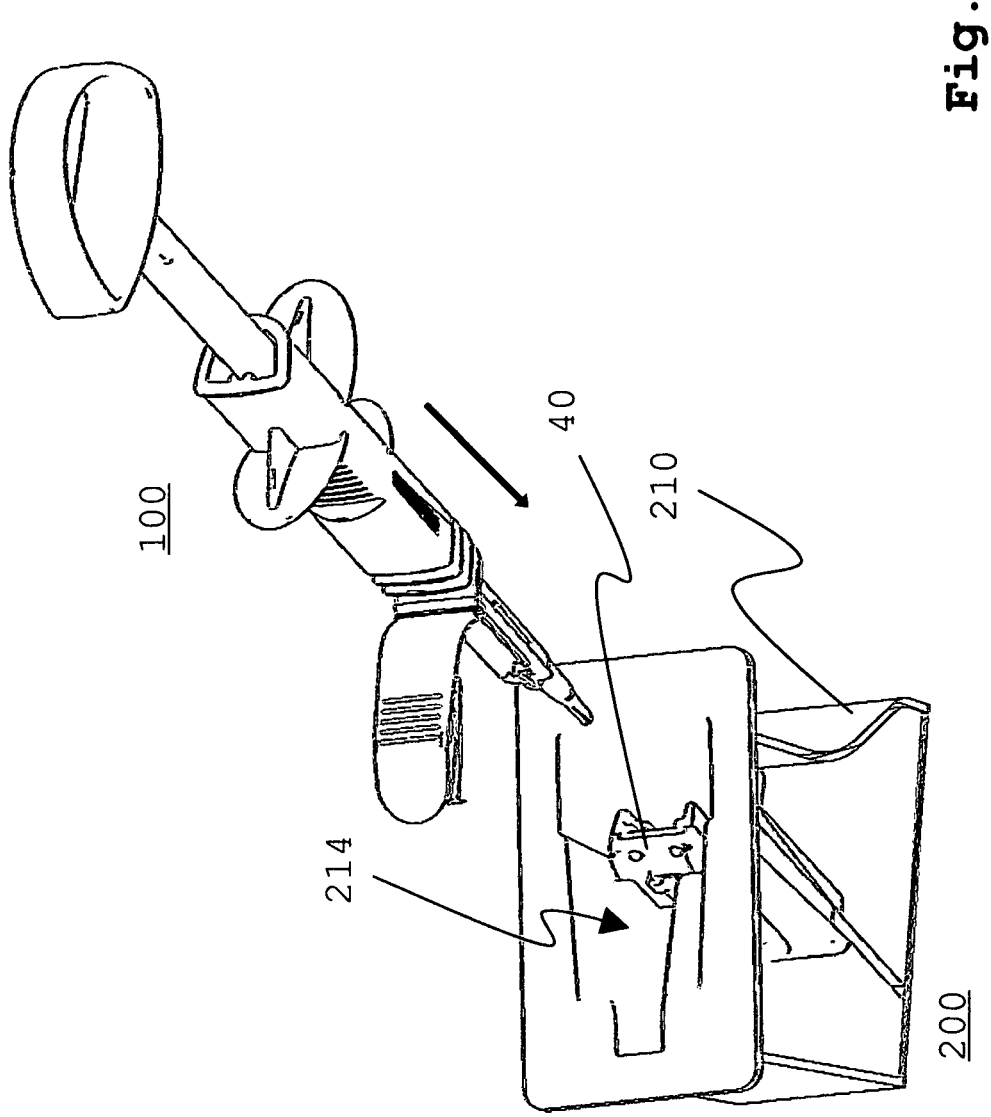
Fig. 6.b

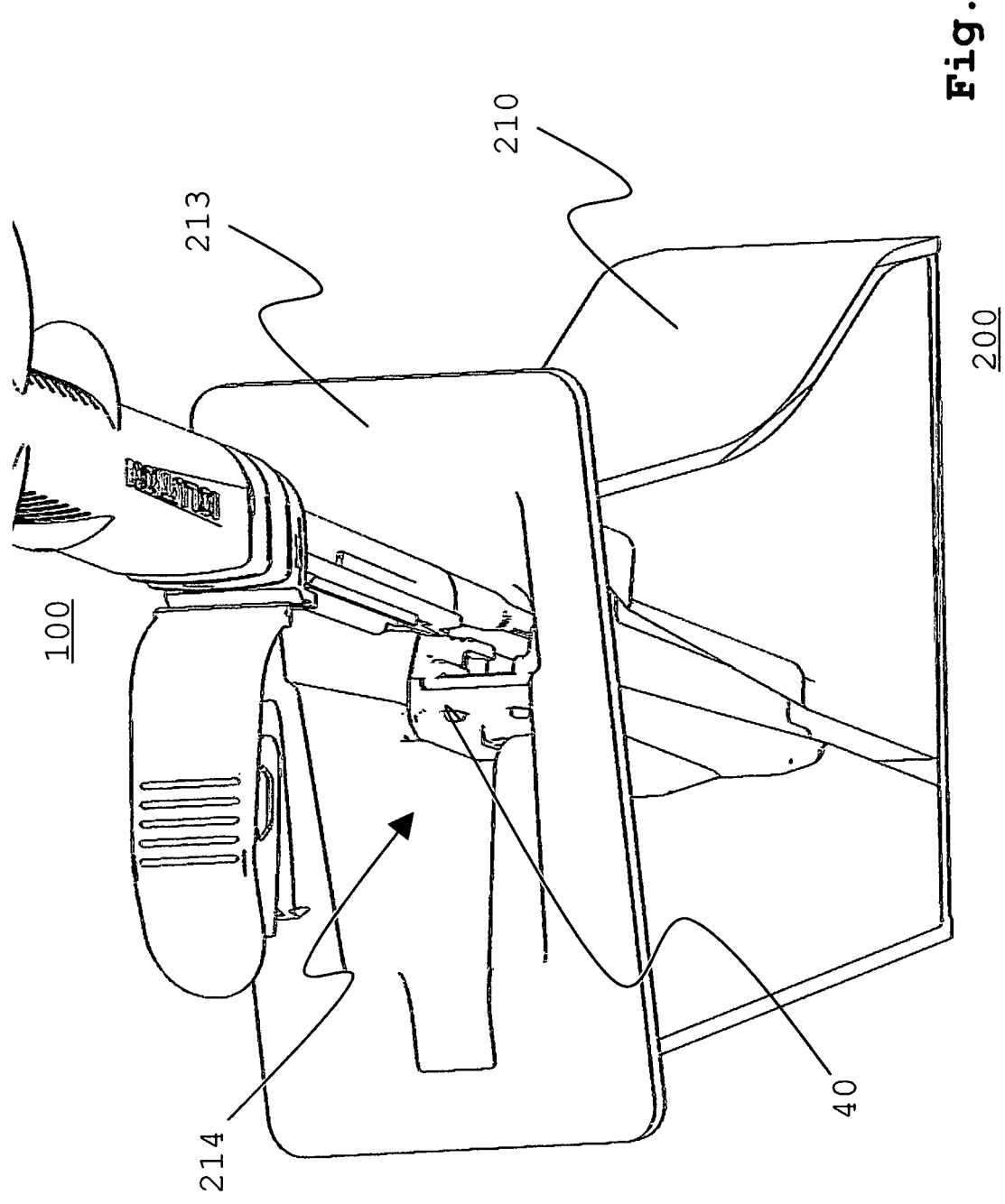
Fig. 6.c

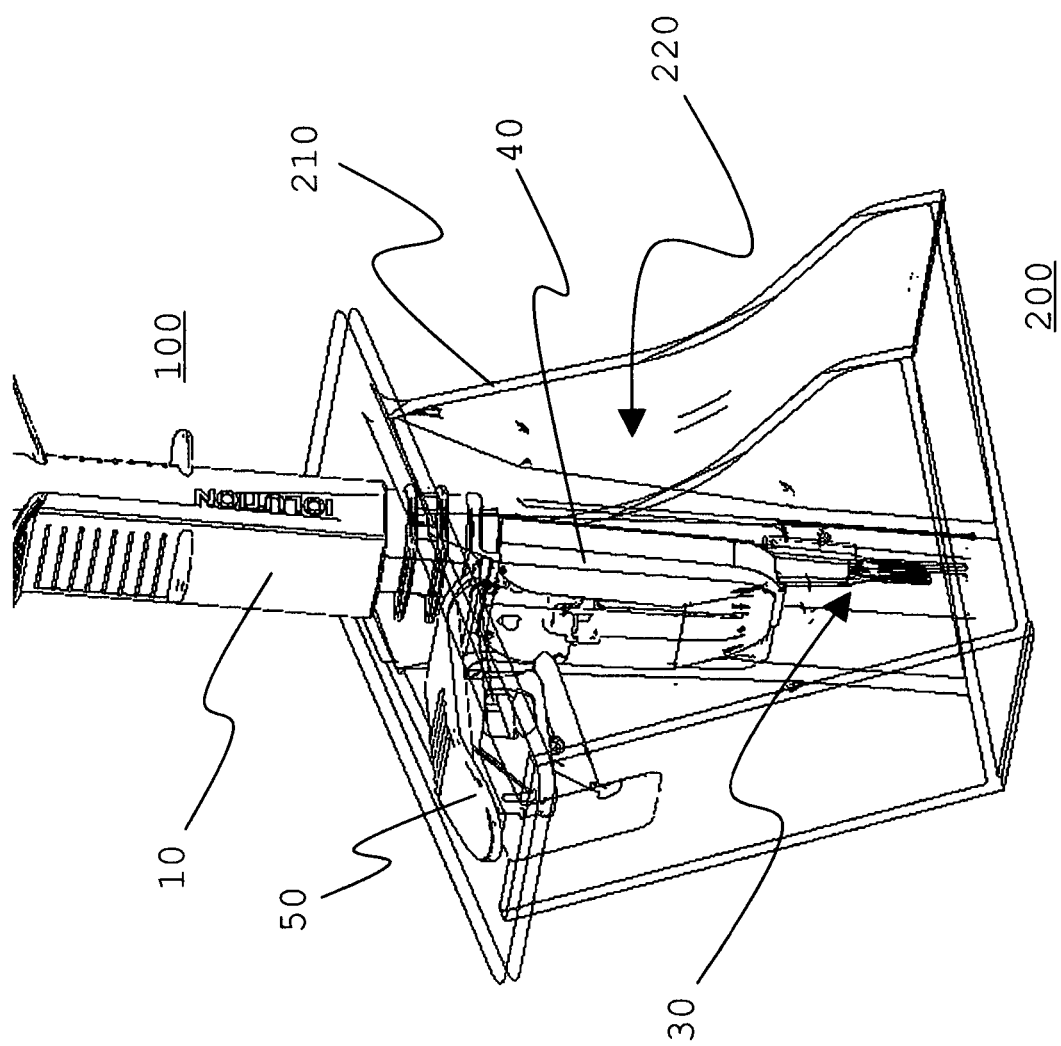
Fig. 6.d

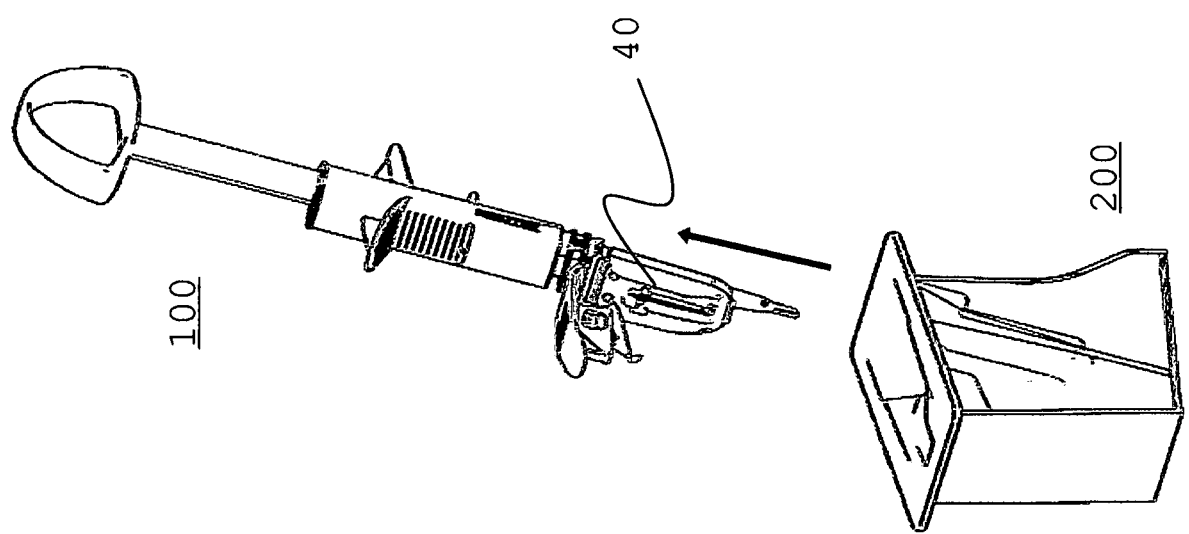
Fig. 6.e

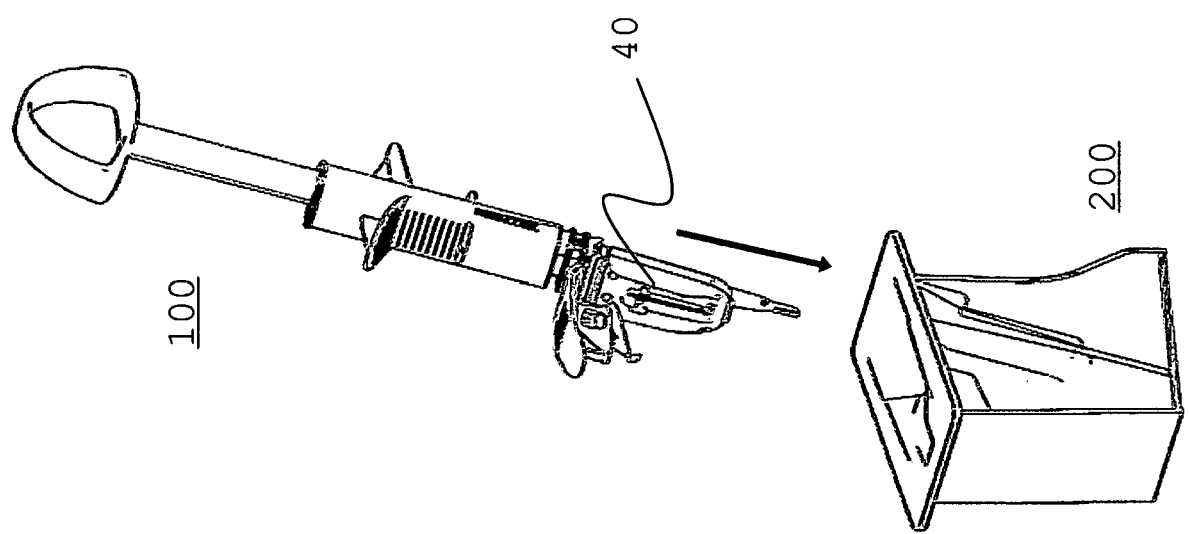

CONTAINER SYSTEM FOR HEATING AN INTRAOCULAR LENS

CROSS REFERENCE TO RELATED APPLICATIONS

This application is a National Stage of International Application No. PCT/DE2015/000191, filed on Apr. 20, 2015, which claims priority to German patent application no. 10 2014 005 719.4, filed on Apr. 22, 2014, the disclosures of which are incorporated by reference in their entirety.

FIELD OF THE INVENTION

The present invention relates to a container system for storing an intraocular lens to be implanted.

BACKGROUND OF THE INVENTION

Intraocular lenses are lens implants or artificial lenses to replace the natural lens of a human eye. They are in particular used to replace the lenses of an eye affected by cloudiness (cataract) of the lens. By surgery, the affected lenses are removed and the intraocular lenses are inserted. Insertion into the eye is accomplished by means of a so-called injector, for example. It is important in this context that the surgical incision through which an intraocular lens is implanted is as small as possible (e.g. about 2.5 mm). This can provide for a fastest possible healing process without complication and possibly also avoids the need for suture.

To be able to implant intraocular lenses which generally have a diameter of about 5 to 7 mm, the lenses must be foldable so as to fit through the small incision of about 2.5 mm.

An injector for folding and inserting a folded lens into the human eye is, for example, described in international patent application WO 2011/155887 A1. The content of this patent application, in particular with respect to the magazine described therein is fully incorporated into the present patent application by reference.

What is described therein is an injector for implanting or inserting a temporarily folded intraocular lens, which injector can be used to insert the folded lens into the lens capsule of the eye through an incision of the required size of about 2.5 mm in the eye.

In one embodiment, the magazine with a lens loaded therein is connected to the injector only shortly before the operation, for loading the injector system. Thus, the lens can be loaded into the magazine in advance, under controlled conditions, for example by a manufacturer of lenses. The loaded magazine may then be stored under sterile conditions in a storage container, for example in a blister package which is preferably filled with a sterile liquid.

GENERAL DESCRIPTION OF THE INVENTION

Against this background described above, the present invention is based on the object to even further improve the introduction of the lens into the eye.

In particular it should be possible to roll up a lens to be implanted even smaller.

These objects are achieved by the container system according to the independent claim. Advantageous embodiments are specified by the subject matter of the dependent claims, the description and/or the drawings.

It has been found that the temperature of the lens plays an important role for the folding of the lens, the insertion of the lens into the eye, and/or for the deployment (unfolding) of the lens. A heated lens is much more supple and flexible and can be rolled up smaller, so that a cut opening (incision) in the eye can be further reduced. Moreover, a warm lens will deploy faster after having been inserted into the eye.

Generally, the invention therefore contemplates to enhance the storage container described in the prior art and briefly referred to as container below, so that it is provided with a heating device.

In detail, the invention provides a container system for heating and/or storing a lens, which comprises the following components: a container for storing at least one lens pre-loaded in a magazine, and a heating device integrated in the container, and/or a connection device for a heating device, for heating the lens pre-loaded in the magazine within the container. Preferably, the lens is an intraocular lens intended to be implanted into the eye.

In contrast to the prior art, the magazine is not placed in a heating bath. Rather, according to a first variant of the invention the container is equipped or produced with the heating device. The heating device is integrated with the container. Heating device and container form a functional unit.

According to a second variant of the invention, the container is not directly equipped with the heating device. The container is provided with the connection device for the heating device. The connection device is integrated with the container. Connection device and container constitute or form a functional unit. The heating device is provided separately in this case. It may for instance be designed as a kind of charging station to which the container can be connected via its connection device.

According to the invention, the lens as such is not stored or storable in the container but rather is pre-loaded in a magazine and/or on the injector. The magazine is or can be placed in the container together with the lens stored in the magazine, optionally together with the injector. In particular, in the first embodiment it is possible in this way to directly connect the magazine to an injector after opening of the container. In the second embodiment it is possible to stably position the pre-loaded injector in the container to be able to heat the magazine and the lens.

In a first embodiment, a magazine including a lens is already disposed in the container in the closed state thereof. In particular, the container system is characterized by the fact that the magazine together with the lens is positioned in the closed container. After opening of the container, the magazine can be connected to the injector. This is particularly suitable for hydrophilic lenses since they are stored in a solution.

Hydrophobic lenses may also be positioned and stored in this manner. However, both types of lenses may as well be disposed and stored outside of the container to be placed and heated in the container indirectly, via the preloaded injector, prior to operation, ready for the operation.

In a second embodiment, the container initially does not contain a lens. However, it may already be filled with a liquid. It is only for heating that the lens pre-loaded in the magazine is introduced into the open container then.

The magazine is introduced into the container together with the lens stored in the magazine and is already pre-mounted on the injector in this case. The container system is characterized such that the magazine together with the lens can preferably be reliably positioned in the open container. The magazine is already connected to the injector in this case. This is particularly suitable for hydrophobic lenses since such lenses can be stored together with the magazine and/or the injector preferably without being immersed in a solution.

In a further embodiment, the container has a receptacle area for the magazine and/or for a portion of the injector. The receptacle area preferably has a shape substantially conforming to the magazine and/or the front portion of the injector. According to one variant, the receptacle area may be substantially tailored for the magazine and/or a portion of the injector. A substantially precisely fitting shape reduces or avoids the risk of damage to the injector, the magazine and/or the lens, in particular when the injector is being inserted into the container.

In one embodiment the container is provided as a stably upright standing container. This reveals a further advantage of the container. It provides a stable support condition for the injector coupled to the magazine, in which condition the now pre-loaded injector can be provided on the operating table ready for use until required by the user.

As already mentioned above, the lens or the lens together with the magazine may in particular be stored in the container in a liquid. An example of such a storage liquid is a sterile saline solution. The liquid volume is, for example, in the order of less than 20 ml, or less than 10 ml, preferably from 4 ml to 5 ml.

The heating device is preferably adapted to heat the lens to a target temperature in a range from about 25° C. or 30° C. to 40° C., preferably from 37° C. to 40° C. This should be possible in particular starting at a starting temperature in a range from about 4° C. to about 25° C. According to one embodiment, the target temperature should be reached after about 30 seconds and/or the target temperature should substantially be maintained over a period of about 1 minute to about 10 minutes.

The container system according to the invention may be provided as a single-use system or as a reusable system. This is in particular dependent on whether the heating device can be recharged after use, for example. Both variants may already contain the lens or may be loaded with the lens before use. This is particularly dependent on whether a hydrophobic or a hydrophilic lens is used.

In one embodiment, the heating device comprises a latent heat storage which may for example be based on saturated salt solutions such as sodium acetate, and/or on paraffin. A latent heat storage has particular advantages in that it is cheap, easy to be integrated, can be operated without external or internal power supply, can moreover be sterilized, e.g. autoclaved, without significant damage, and/or may even be reused. In particular, the latent heat storage can be recharged during sterilization, in particular by autoclaving, without separate heat supply.

According to another embodiment of the heating device, it comprises an electric heating device. The power supply required therefore should preferably be provided by a battery or an accumulator. Preferably, the power supply should not be provided by an external power supply. This type of heating in particular provides the advantage that a precise target temperature can be maintained over a prolonged period.

The heating device may be disposed on an outer surface of the container. The heating device is, for example, provided as a kind of charging station into which the container can be introduced and heated. In this embodiment, the heating device is connectable to the container via the connection device thereof.

In a preferred embodiment, the heating device is arranged on an outer surface of the container. In one embodiment, for example, the heating device is integrated with the container. This allows to provide a compact system.

Preferably, the heating device has a switch for being activated. The heating device may be configured to be activated manually or automatically.

In one embodiment, the heating device and the container are coupled or can be coupled to each other in a manner so that the heating device is activated or turned on when the container is being opened. In another embodiment, the heating device and the lid of the container are coupled or can be coupled to each other so that upon opening or removal of the lid, the heating device is activated.

As already mentioned above, in one embodiment the container or the container system is configured so as to stand stably even if the injector is connected to the magazine.

In particular for improving the stability and/or handling of the container system, the lower surface of the container has a larger cross section than a central region of the container.

In a first embodiment, the container has a preferably substantially planar lower surface and/or an upper surface inclined relative to the lower surface.

In a second embodiment, the container has a preferably substantially planar first side wall that is inclined relative to the lower surface, and/or a second side wall opposed to the first side wall, which is inclined relative to the lower surface and preferably has a step. In particular due to the step the containers can be reliably held by the user when tearing off the lid. Preferably, the planar side wall and the lower surface enclose an angle $\alpha 1$ of $90°<\alpha 1 \leq 120°$.

In a third embodiment, a longitudinal axis L of the receptacle area is inclined relative to the lower surface of the container. Preferably in that case, the longitudinal axis L of the receptacle area and the lower surface enclose an angle $\alpha 2$ of $90°>\alpha 2>60°$.

The container system of the invention may be used for storing one lens alone, a magazine including the lens, and/or even an entire injector system. The dimensions and/or shapes of the container systems are dependent, inter alia, on the design of an intraocular lens to be implanted and/or of a magazine. The container system is for instance suitable for all soft foldable intraocular lenses. Such lenses are, for example, composed of acryl, silicone, and/or hydrogel. The container system may be used for hydrophilic lenses, in particular those having a water content from 22% to 50%, and/or for hydrophobic lenses which are usually less flexible.

For specifying the dimensions, the following parameters are introduced (for this see FIGS. 4.c and 4.d): height Z, length Y, and width X. To obtain a compact container system, the following values are possible, for example: 20 mm$\leq$X$\leq$50 mm, preferably 30 mm$\leq$X$\leq$40 mm, and/or 60 mm$\leq$Y$\leq$100 mm, preferably 75 mm$\leq$Y$\leq$85 mm, and/or 50 mm$\leq$Z$\leq$90 mm, preferably 60 mm$\leq$Z$\leq$80 mm.

In a further embodiment of the invention, the container and/or the magazine are made substantially transparent. This in particular permits to visually check the insertion of the injector into the container and/or into the magazine.

The heating device and/or the connection device for the heating device may be provided in integrated form in and/or on the container. However, it is also possible to retrofit conventional containers with a heating device according to the invention and/or with a connection device according to the invention for a heating device.

Therefore, a kit for retrofitting a container for assembling a container system according to at least one of the embodiments described above is also within the scope of the invention. The kit comprises a heating device connectable to the container and/or connection device for a heating device connectable to the container for heating a lens pre-loaded in a magazine within the container.

BRIEF DESCRIPTION OF THE DRAWINGS

The present invention will now be described in more detail by way of the following exemplary embodiments. For this purpose, reference is made to the accompanying drawings. The same reference numerals in the individual drawings refer to the same parts.

FIGS. 3.a and 3.b are perspective exterior views illustrating the connection of the container to a non-integrated heating device.

FIGS. 4.a to 4.d are different views illustrating the container in which the magazine is stored.

FIGS. 5.a and 5.b are perspective views illustrating the injector system preferably pre-loaded with a magazine in a condition introduced in the container system (transparently shown here).

FIGS. 6.a to 6.e are perspective views illustrating the insertion of an injector into the container system pre-loaded with a magazine and removal thereof.

FIG. 7 is a perspective view illustrating the insertion of an injector pre-loaded with a magazine into the empty containers system.

DETAILED DESCRIPTION OF THE INVENTION

Figure 1:
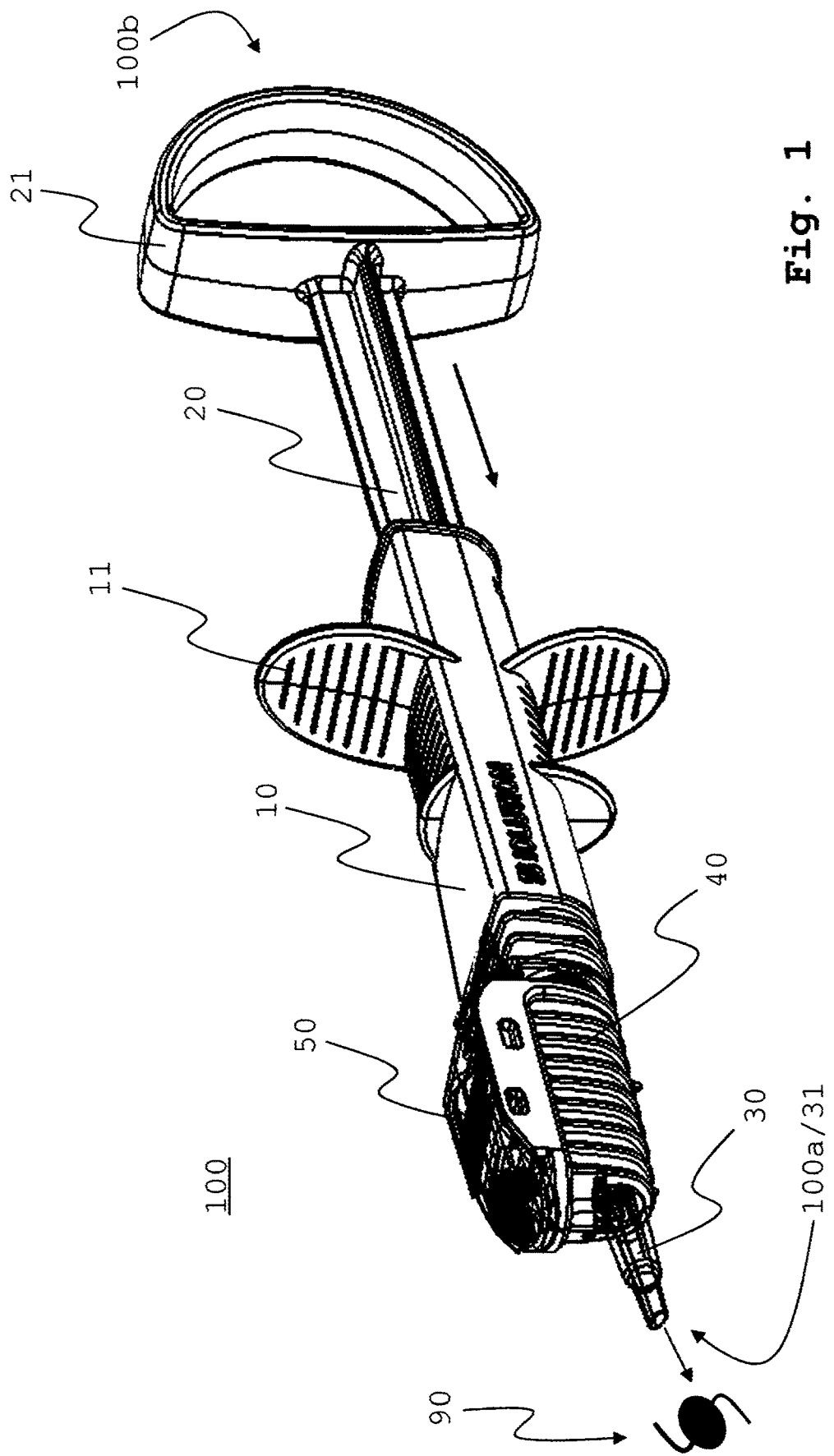
FIG. 1 shows an injector system in its assembled state with loaded magazine.

FIG. 1 shows an injector system 100 in its assembled state. The modules that make up the injector system 100 include a housing 10, a slider 20, a needle 30, and a magazine 40.

The magazine 40 is placed on the needle 30, preferably plugged thereto. For example, needle 30 and magazine 40 are snap-connected to each other. Magazine 40 is preferably loaded with a lens 90, and lens 90 is secured in the magazine 40 by retaining flap 60 before the magazine 40 is mounted to the injector 100 or the needle 30, respectively (for this see FIG. 2).

Prior to an initial operation of the injector 100, first the storage container 210 is opened. For this purpose, the lid 211 is peeled off from the end faces 213, for example (for this see FIG. 2). The magazine 40 is mounted to the needle 30 in this case by dipping the injector 100 into the storage container 210, at least the needle 30 thereof, and plugging the magazine 40 to the needle 30. This offers the advantage that the sterile conditions are maintained for prolonged periods and that the transport channel of the needle 30 is wetted with the storage liquid 212, so that the lens 90 and the slider 20 will slide better in the needle 30.

Figure 2:
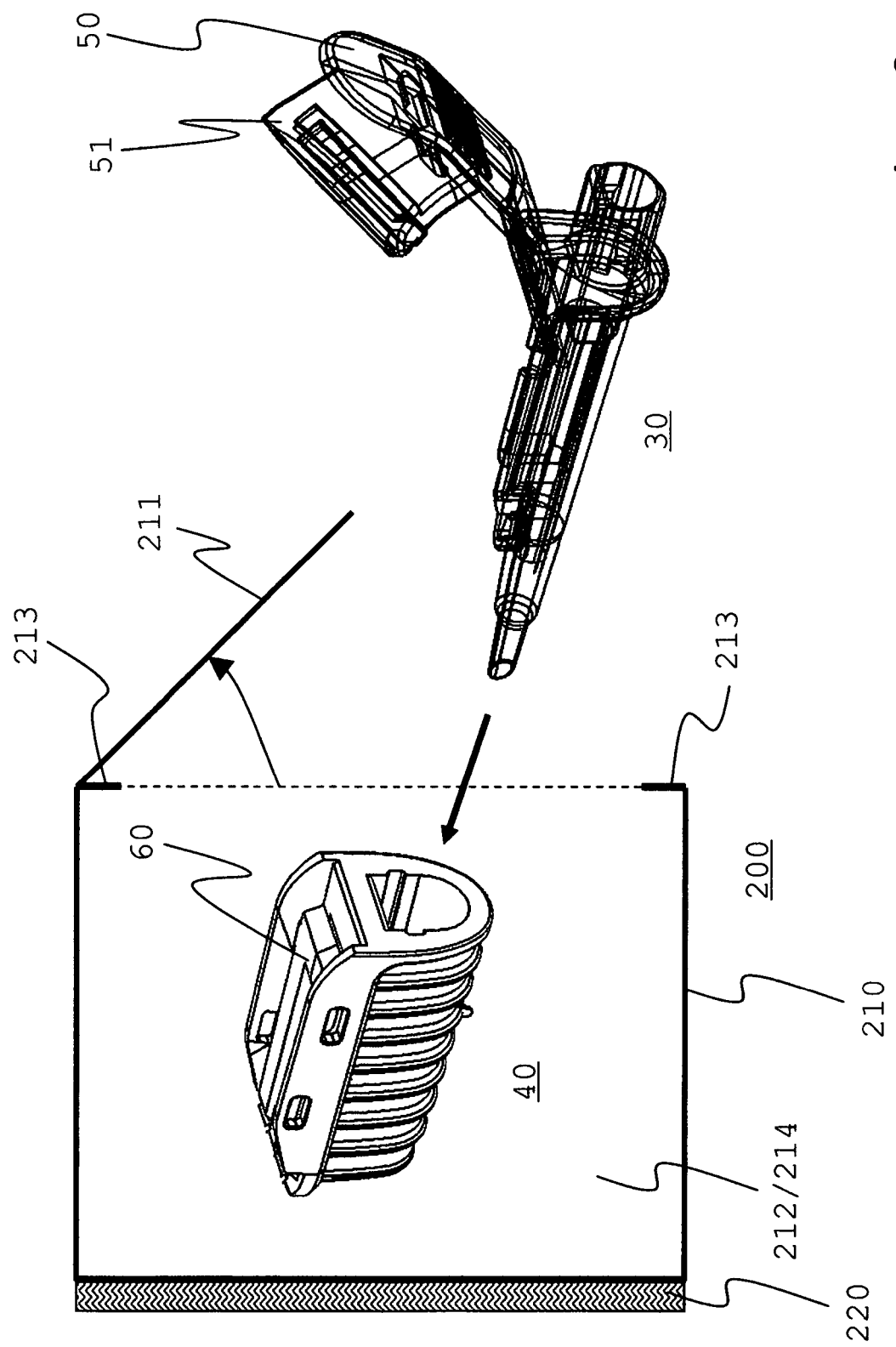
FIG. 2 is a perspective exterior view illustrating the loading of the injector system with the magazine which is contained in a schematically illustrated container with integrated heating device.

Furthermore, FIG. 2 schematically illustrates the heating device 220 according to the invention. By way of example, a container system 200 according to a first embodiment is illustrated comprising a container 210 with integrated heating device 220. The heating device 220 is disposed on the outer surface of container 210. The heating device 220 is integrated with the container 210. Container 210 and heating device 220 constitute or form a functional unit. For example, the material for a latent heat storage may be filled in a cavity of the container 210, for example on the left and/or right side, and in particular a small metal plate (not shown) may be incorporated in the outer wall of the container 210. The small plate performs the function of a switch. By pressing the small plate, heating is initiated. Activation may for example as well be effected when the lid 211 is opened, by some sort of coupling not shown in the figures. Preferably, the invention provides a container system 200 for storing a lens 90, which comprises a container 210 with at least one lens 90 stored in the container 210, and with a heating device 220 for heating the lens 90 within the container 210. The heating by heating device 220 is achieved through the container 210.

FIG. 2 illustrates the heating device 220 as a unit preferably permanently connected to the container 210. However, heating device 220 may as well be provided as a kind of kit which can be used for retrofitting a conventional container 210, which is however not shown in the figures.

FIGS. 3.a and 3.b show a container system 200 according to a second embodiment, comprising a container 210 with integrated connection device 221 for a non-integrated heating device 220. The heating device 220 is provided, for example, as a kind of charging station to which the container 210 can be connected via its connection device 221 and then heated. To this end, the container 210 is, for example, moved toward heating device 220 (FIG. 3.a). FIG. 3.b shows the final connected state.

The figures show the connection device 221 as a unit preferably permanently connected to the container 210. However, connection device 221 may as well be provided as a kind of kit, in particular in combination with the heating device 220, which can be used for retrofitting a conventional container 210, which is however not shown in the figures.

FIGS. 4.a to 4.d show different perspectives of an empty container 210 for a magazine 40. The container 210 is shown in different perspectives with the lid 211 already peeled off. The container 210 is designed as an upright standing item 210. The upright standing item 210 serves to support or temporarily store the preloaded injection system 100 (for this see also FIGS. 5.a and 5.b). The magazine 40 can be mounted onto the injector 100 by inserting the injector 100 into the container 210. The side walls have recesses in which a heating device 220 may be placed, which is not shown here. The material of the container 210 comprises for instance polypropylene. The lid 211 is for instance provided by a metal, preferably aluminum. Such a closed container system 200 comprising container 210 and a latent heat storage as a heating device 220 furthermore meets the requirements of autoclaving. The lid may as well be omitted or may be semipermeable so as to meet the requirements of further sterilization methods, such as, e.g., ethylene oxide (EtO) or gamma radiation.

FIGS. 4.c (perspective side view) and 4.d (top 216 plan view) show the dimensions of a container system 200 according to the invention. For this purpose, height Z, length Y, and width X are introduced here. In particular in order to provide a compact container system 200, the following values are possible: 33 mm≤X≤37 mm and/or 77 mm≤Y≤83 mm and/or 67 mm≤Z≤71 mm. In FIG. 4.d, the Z-axis extends perpendicularly to the sheet plane.

In particular to improve stability and/or handling, the upper surface 216 and side walls 217 and 218 are inclined with respect to the lower surface 215 of the container 200. Side wall 217 is inclined by an angle α1 with respect to the lower surface 215. An upper portion of side wall 218 is also inclined by the angle α1 relative to the lower surface 215. Preferably, 95°≤α1≤110°. Furthermore, the longitudinal axis L of the receptacle area 214 is inclined relative to the lower surface 215 by an angle α2. Angle α2 is preferably 85°>α2>75°.

The lower surface 215 of container 210 has a larger cross section than a central region of the container 210. In particular to this end, a step 219 is provided in side wall 218. Due to the laterally projecting step 219 the container 210 can be safely held by a user.

FIGS. 5.a and 5.b illustrate the container system 200 with inserted magazine 60 and injector 100. Container 210 is designed as an upright standing item. It stands stably. That is to say, with or without the injector 100 inserted, the center of gravity perpendicular of the container system will intersect with the bearing surface of the container system 200 and/or the bearing surface of the container 210. The container system with the injector inserted can for instance be provided on the operating table ready for use and stably. The magazine 60 together with the lens 90 may have already been contained in the closed container 210.

After opening of the container 210 the injector 100 was then introduced into the magazine (for this see FIGS. 6.a to 6.e). However, it is as well possible that the closed container 210 was initially provided without lens 90. The magazine 60 was then introduced into the opened container 210 together with the lens 90 and the injector 100, for being heated (for this see FIG. 7). FIGS. 5.a and 5.b illustrate a further advantage. In addition to the heating of the lens 90 to increase flexibility thereof, the needle 30 is also heated to the target temperature. The so enhanced flexibility of the needle 30 in turn contributes to an improvement in the surgical process by allowing for a smaller incision and facilitating the introduction of otherwise less flexible lenses 90. This may further be promoted by using slide-enhancing processes. The latter may be achieved by a coating or blooming process.

Finally, FIGS. 6.a to 7 again illustrate different configurations in which the container system 200 may be provided or operated.

First, FIGS. 6.a to 6.e show the introduction of an injector 100 into a container system 200 which is pre-loaded with a magazine 40. FIG. 6.a shows the container 210 with the lid 211 already peeled off. FIG. 6.b moreover illustrates the injector 100 which is inserted into the container 210 and the magazine 40 in the direction of the arrow. FIG. 6.c shows an enlarged view of the approached injector 100, shortly before connection. FIG. 6.d corresponds to FIG. 5.b and shows the injector 100 in the state connected to magazine 40. It can be seen that not only the magazine 40 is received in the receptacle area 214. A portion of the injector is also received in the receptacle area 214, here the needle 30 and/or the folding body 51, by way of example. FIG. 6.e illustrates retraction of the injector 100 now loaded with the magazine 40. This variant is particularly suitable for hydrophilic lenses, but also for hydrophobic lenses 90.

Finally, FIG. 7 illustrates an empty container system 200. In this case, the container 210 is not pre-loaded with a magazine 40. By contrast, the injector 100 is already loaded with a magazine 40 here. The so pre-loaded injector 100 is introduced into the container 210 with its front end, in the direction of the arrow, for heating the lens 90 stored the magazine 40. Container 210 may be empty or may be filled with a liquid 212, for example. In the latter case, the container 210 may have been filled with the liquid 212 already beforehand or may have been filled with the liquid 212 after having been opened. This variant is particularly suitable for hydrophobic lenses 90.

It will be apparent to those skilled in the art that the above embodiments have been described by way of example only. The invention is not limited to these embodiments but may rather be modified in many ways without departing from the spirit of the invention.

Features of individual embodiments may be combined with each other as well as with the features mentioned in the general part of the description.

LIST OF REFERENCE NUMERALS

10 Injector body, or injector housing, or housing, or handset
11 Handle on injector body
20 Slider, or plunger, or lens slider
21 Handle, or slider handle
30 Needle, or tube for insertion into the eye, or body for discharging the lens
31 Transport channel or advance channel
40 Magazine or container for storing the lens
50 Folding flap, or folding plate support, or flap
51 Folding body, or folding plate, or folding rib
60 Retainer, or retaining flap, or flap
90 Lens, or intraocular lens
100 Injector, or injector system, or applicator
100a Front end of injector
100b Rear end of injector
200 Container system
210 Container
211 Lid of container
212 Storage liquid
213 Engagement surface for container lid
214 Receptacle area for the magazine in the container and/or for a front portion of the injector
215 Lower surface of the container
216 Upper surface of the container
217 First, preferably flat side wall of the container
218 Second side wall of the container
219 Step or kink in second side wall
220 Heating device
221 Connection device for heating device

The invention claimed is:

1. A container system (200) for heating and storing an intraocular lens (90) to be implanted in an eye by an injector, comprising:
   a container (210) for storing at least one lens (90) pre-loaded in a magazine (40) wherein the container system (200) is configured so as to stand stably;
   a lid (211) capable of being opened or removed for introducing an injector body (10) into the container (210); and
   a heating device (220) integrated in the container (210) for heating the lens (90) within the container (210),
   wherein the magazine (40) together with the lens (90) are contained in the container (210) within a sterile liquid while the lid (211) is closed, and
   wherein the injector body (10) located outside of the container (210) is introduced into the container (210) in an open position and connected to the magazine (40) containing the heated lens (90) after opening the container (210) to jointly form the injector (100).

2. The container system (200) according to claim 1, wherein the heating device (220) is adapted to heat the stored lens (90) to a temperature in a range from 25° C. to 40° C.

3. The container system (200) according to claim 1, wherein the heating device (220) comprises a latent heat storage and/or an electric heating device.

4. The container system (200) according to claim 1, wherein the heating device (220) is arranged or can be arranged on an outer surface of the container (210).

5. The container system (200) according to claim 1,
wherein the heating device (220) comprises a switch for being activated; and/or
wherein the heating device (220) can be activated manually and/or automatically.

6. The container system (200) according to claim 1, wherein the heating device (220) and the container (210) are coupled or can be coupled to each other in a manner so that the heating device (220) is activatable upon connection or opening of the container (210).

7. The container system (200) according to claim 1, wherein the heating device (220) and a lid (211) of the container (210) are coupled or can be coupled to each other so that the heating device (220) is activatable upon opening of the lid (210).

8. The container system (200) according to claim 1, wherein a lower surface (215) of the container (210) has a larger cross section than a central region of the container (210).

9. The container system (200) according to claim 1, wherein the container (210) has a planar lower surface (215) and/or an upper surface (216) inclined relative to the lower surface (215).

10. The container system (200) according to claim 1, wherein the container (210) has a planar first side wall (217) that is inclined relative to the lower surface (215), and/or a second side wall (218) that is inclined relative to the lower surface (215) and has a step (219).

11. The container system (200) according to claim 1, wherein the container (210) has a receptacle area (214) for the magazine (40) and/or for a portion of the injector body (10) substantially conforming to the magazine (60) and/or to the portion of the injector body (10).

12. The container system (200) according to claim 11, wherein a longitudinal axis (L) of the receptacle area (214) is inclined relative to the lower surface (215) of the container (210).

13. The container system (200) according to claim 1, wherein the container (210) and/or the magazine (40) is/are transparent.

14. The container system (200) according to claim 1,
wherein the injector (100) includes the injector housing (10) and a slider (20).

15. The container system (200) according to claim 1,
wherein the container (210) is a blister package.

16. The container system (200) according to claim 1,
wherein the lid (211) is made of aluminum and designed to be peeled off a face of the container.

17. The container system (200) according to claim 1, wherein the liquid (212) a sterile saline solution having a volume of less than 10 ml.

18. A container system for heating and storing an intraocular lens before being implanted in an eye by an injector, comprising:
a container for storing a magazine with a pre-loaded lens therein in a sterile liquid;
a removable lid arranged to close the container; and
a heating device integrated in the container for heating the lens within the container,
wherein the container is designed to be opened by peeling off the removable lid,
wherein the container is designed to receive an injector body for connecting the magazine containing the heated lens to the injector body after the removable lid has been peeled off, and
wherein the injector body and the magazine jointly form the injector.

* * * * *